United States Patent
Cherukuri et al.

(10) Patent No.: US 6,482,465 B1
(45) Date of Patent: *Nov. 19, 2002

(54) POSITIVE HYDRATION METHOD OF PREPARING CONFECTIONERY AND PRODUCT THEREFROM

(75) Inventors: Subraman R. Cherukuri, Vienna, VA (US); Francisco Zamudio-Tena, Westwood, MA (US); Claude Bayard, Arlington, VA (US); Supapong Siris, Chantilly, VA (US); Amrik Khurana, Granada Hills, CA (US); Sambasiva Ghanta, Vienna, VA (US); Matthew J. Strait, Arlington, VA (US); Martin K. Schaller, Fairfax, VA (US); David M. Teale, Falls Church, VA (US); Peter King, Herndon, VA (US); Robert K. Yang, Flushing, NY (US); T. Victor Oh, Annandale, VA (US)

(73) Assignee: Biovail Technologies Ltd., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,213

(22) Filed: May 26, 2000

(Under 37 CFR 1.47)

Related U.S. Application Data

(63) Continuation-in-part of application No. 09/149,597, filed on Sep. 8, 1998, now abandoned, and a continuation-in-part of application No. 09/110,713, filed on Jul. 7, 1998, now abandoned, and a continuation-in-part of application No. 09/092,775, filed on Jun. 5, 1998, now abandoned, and a continuation-in-part of application No. 09/046,186, filed on Mar. 23, 1998, now abandoned, and a continuation-in-part of application No. 08/881,853, filed on Jun. 24, 1997, now abandoned.

(51) Int. Cl.$^7$ ................................................. A23G 3/00
(52) U.S. Cl. ..................... 426/660; 426/658; 426/572
(58) Field of Search .................. 426/660, 658, 426/572

(56) References Cited

U.S. PATENT DOCUMENTS

| | | | |
|---|---|---|---|
| 2,171,244 A | 8/1939 | Otterbacher | 99/130 |
| 2,466,146 A | 4/1949 | Baker | 99/131 |
| 2,520,581 A | 8/1950 | Turner et al. | 99/134 |
| 2,651,574 A | 9/1953 | Whittler | 99/134 |
| 3,908,032 A | 9/1975 | Didelot et al. | 426/660 |
| 3,930,052 A | 12/1975 | De Brou et al. | 426/576 |
| 4,089,987 A | 5/1978 | Chang | 426/564 |
| 4,097,616 A | 6/1978 | Guillou et al. | 426/548 |
| 4,230,687 A | 10/1980 | Sair et al. | 424/22 |
| 4,238,519 A | 12/1980 | Chang | 426/549 |
| 4,307,124 A | 12/1981 | Moirano | 426/573 |
| 4,344,972 A | 8/1982 | Wienecke | 426/103 |
| 4,545,989 A | 10/1985 | Becker et al. | 424/154 |
| 4,582,709 A | 4/1986 | Peters et al. | 426/74 |
| 4,724,136 A | 2/1988 | Scheibl | 424/50 |
| 4,778,676 A | 10/1988 | Yang et al. | |
| 4,790,991 A | 12/1988 | Shaw et al. | |
| 4,797,288 A | 1/1989 | Sharma et al. | |
| 4,847,090 A | 7/1989 | Della Posta et al. | |
| 4,855,326 A | 8/1989 | Fuisz | |
| 4,867,989 A | 9/1989 | Silva et al. | |
| 4,882,152 A | 11/1989 | Yang et al. | |
| 4,882,154 A | 11/1989 | Yang et al. | |
| 4,882,160 A | 11/1989 | Yang et al. | |
| 4,980,178 A | 12/1990 | Cherukuri et al. | |
| 5,059,416 A | 10/1991 | Cherukuri et al. | |
| 5,073,389 A | 12/1991 | Wienecke | |
| 5,238,696 A | 8/1993 | Fuisz | |
| 5,262,191 A | 11/1993 | Chakraborty et al. | |
| 5,279,849 A | 1/1994 | Fuisz et al. | |
| 5,348,758 A | 9/1994 | Fuisz et al. | |
| 5,389,395 A | 2/1995 | Joseph et al. | |
| 5,429,836 A | 7/1995 | Fuisz | |
| 5,462,760 A | 10/1995 | Serpelloni et al. | |
| 5,498,439 A | 3/1996 | Bonner | |
| 5,501,858 A | 3/1996 | Fuisz | |
| 5,518,551 A | 5/1996 | Battist et al. | |
| 5,580,601 A | 12/1996 | Ribadeau-dumas et al. | |
| 5,582,855 A | 12/1996 | Cherukuri et al. | |
| 5,587,172 A | 12/1996 | Cherukuri et al. | |
| 5,587,189 A | * 12/1996 | Cherukuri et al. | 426/660 |
| 5,587,198 A | 12/1996 | Cherukuri et al. | |
| 5,622,717 A | 4/1997 | Fuisz | |
| 5,637,311 A | 6/1997 | Pallenberg | |
| 5,637,313 A | 6/1997 | Chau et al. | |
| 5,654,003 A | 8/1997 | Fuisz et al. | |
| 5,690,990 A | 11/1997 | Bonner | |
| 5,804,247 A | 9/1998 | Cherukuri et al. | |
| 5,824,342 A | 10/1998 | Cherukuri et al. | |
| 5,858,391 A | 1/1999 | Cuca et al. | |
| 5,879,728 A | 3/1999 | Graff et al. | |

FOREIGN PATENT DOCUMENTS

| | | |
|---|---|---|
| EP | 0 155 203 B1 | 1/1992 |
| EP | WO 93/11750 | 6/1993 |
| EP | 0 753 296 A2 | 1/1997 |
| WO | WO 98/58549 | * 12/1998 |
| WO | WO 99/48379 | * 9/1999 |

OTHER PUBLICATIONS

Alikonis; "Candy Theology"; 1979, AVI Publishing Company, Inc., pp. 95–107.

Minifie; "Chocolate, Cocoa and Confectionery: Science and Theology Second Edition"; AVI Publishing Company, Inc., pp. 424 and 425.

* cited by examiner

Primary Examiner—Nina Bhat
(74) Attorney, Agent, or Firm—Pillsbury Winthrop LLP; Robin L. Teskin

(57) ABSTRACT

A method of producing a chewy confectionery involves high or low shear mixing with no cooking to produce a mass which is well hydrated and yet has no phase separation of moisture. A bioaffecting agent included in the confectionery is effectively taste-masked, even one that is typically organoleptically unpalatable.

32 Claims, No Drawings

POSITIVE HYDRATION METHOD OF PREPARING CONFECTIONERY AND PRODUCT THEREFROM

This application is a continuation-in-part of
(1) U.S. application Ser. No. 08/881,853 filed Jun. 24, 1997, abandoned, and a continuation-in-part of
(2) U.S. application Ser. No. 09/046,186 filed Mar. 23, 1998, abandoned, and a continuation-in-part of
(3) U.S. application Ser. No. 09/092,775 filed Jun. 5, 199, abandoned, and a continuation-in-part of
(4) U.S. application Ser. No. 09/110,713 filed on Jul. 7, 1998, abandoned, and a continuation-in-part of
(5) U.S. application Ser. No. 09/149,597 filed Sep. 8, 1998, abandoned.

FIELD OF THE INVENTION

The present invention relates to confectioneries, and more particularly to a method of producing a chewy nougat confectionery delivery system for actives in which a fully functionalized mass is obtained without cooking and thus exposing the ingredients therein to high heat. The invention also relates to the novel confectionery systems so produced.

BACKGROUND OF THE INVENTION

The present invention relates to the art of unique delivery systems for comestibles, especially to confectionery manufacturing and particularly to novel methods of making a functionalized confectionery mass which do not require cooking to dehydrate and products therefrom. More particularly, the invention relates to comestible delivery systems, uncooked confectioneries and nougats, and methods for making same.

It is generally considered a necessity in the art of preparing food or drug delivery systems like confectionery masses such as nougats to use water as a mixing medium and source of hydration for ingredients. Specifically with respect to nougats, a typical recipe calls for soaking egg albumen in water over a period of time, such as overnight, in order to fully hydrate the protein. Following hydration the egg albumen is stirred and strained before being beaten into a stiff foam. Other ingredients such as sugar, honey, and corn syrup are separately cooked with water to a relatively high cooking temperature of from about 135° C. to about 138° C. to achieve the necessary interaction among the ingredients. The cooked mixture is then poured into the egg and beaten with a nougat mixer, which is similar to a marshmallow mixer but generally more robust. Additional parts of sugar and other ingredients must then be added and the mixture beaten or stirred over a hot water bath. This conventional nougat preparation method requires cooking the ingredients and using a significant amount of water to serve as a mixing medium and source of hydration. The amount of water used is much larger than that which would permit the formation of the solid nougat. Consequently, the excessive moisture must be driven off as much as possible to achieve the structural integrity and consistency necessary for the end product.

Conventional art processes require excessive amounts of water to provide a mixing medium and to hydrate the components. With respect to hydration, water is supplied in more than sufficient quantity to ensure that specific ingredients are wetted and functionalized. With respect to use of water as a mixing medium, once again an excessive amount of moisture is generally used so that ingredients can be contacted by suspension or dissolution in the medium. The overall process requires the use of far more moisture than is actually required to provide solubility of the ingredients. Unless the water is forcibly removed, the process will result in an incoherent product having no significant structural integrity.

A consequence of using excessive water to hydrate and as a mixing medium is that the artisan must then reduce the unwanted additional moisture. This is generally undertaken by a combination of mixing and boiling to drive off the moisture and bring the mass to proper viscosity and consistency. This process, however, can be highly energy-inefficient and very costly as it requires heat, excessive handling of nougat masses, flashing off of some critical fluids, and an inability to incorporate heat sensitive materials, as well as a less desirable overall stability of the product. Moreover, it is not effective in completely eliminating a substantial amount of the moisture contained in the confectionery mass.

One of the unwanted results of inefficient dehydration is that water remains as a separate phase in the end product. This water is not bound to other ingredients and can be referred to as free moisture or unbound water. Free moisture can detract from the end product because it weakens the structural integrity and/or reduces the quality of organoleptic perception. Moreover, excessive free moisture results in higher water activity, and thereby provides an environment in which microorganisms can grow. Microbiological growth in food products has also been used to measure the existence of free moisture.

Free moisture has been identified in food art by the term water activity. Water activity is defined as the ratio of the vapor pressure of water in an enclosed chamber containing a food to the saturation vapor pressure of water at the same temperature. Water activity is an indication of the degree to which unbound water is found and, consequently, is available to act as a solvent or to participate in destructive chemical and microbiological reactions.

Many food preservation processes attempt to eliminate spoilage by lowering the availability of water to microorganisms. Reducing the amount of free moisture or unbound water also minimizes other undesirable chemical changes which can occur in foods during storage. The processes used to reduce the amount of unbound water in foods include techniques such as concentration, dehydration, and freeze-drying. These processes often require intensive expenditure of energy and are not cost efficient.

In addition, the goal of producing an acceptable chewy nougat confectionery has been further complicated by the inclusion of one or more active substances such as bioaffecting agents or nutrients. Many of these substances are not only heat-sensitive, but also possess undesirable organoleptic features in the sense that they are bad tasting, have a disagreeable odor, or are difficult to chew or swallow. Of further complication is the fact that many of these actives are extremely difficult to blend into an edible delivery system. Often they are simply not physically compatible with one or more of the confectionery ingredients.

Various attempts have now been made to formulate acceptable confectionery systems containing actives. For example, Yang et al., U.S. Pat. Nos. 4,778,676, 4,882,152 and 4,882,154, describe a chewable delivery system comprising a gummy confectionery in which an active is first pre-coated with large amounts of oleaginous material.

Chau et al., U.S. Pat. No. 5,637,313, is directed to a soft, chewable dosage form in which maltitol syrup (HSH) must be utilized. The dosage forms are described as chewing gums, hard candy, cough drops and breath fresheners.

Peters et al., U.S. Pat. No. 4,582,709, relates to a chewable mineral supplement in which corn syrup, sugar, an edible polyol, water and a mineral supplement are combined.

Becker, U.S. Pat. No. 4,545,989, describes a chewable comestible product having a frappe component and a syrup component.

Fuisz, U.S. Pat. Nos. 5,804,247 and 5,587,198, are directed to a confectionery system which is formed by first flash-flow processing of saccharide material in a centrifugal spinning machine under high heat conditions. The resultant flash-flow processed material is then admixed with a well-hydrated hydrobinder such as gelatin.

Sharma et al., U.S. Pat. No. 4,797,288, is directed to a drug delivery system including a core material containing an active and a hydrophobic matrix coating.

Shaw et al., U.S. Pat. No. 4,790,991, relates to an ingestible aggregate containing a pre-swelled substantially anhydrous hydrocolloid and a substrate.

Many of the foregoing references, however, have not always proven wholly successful in providing both a suitable confectionery delivery system, and an acceptable, cost-efficient method of production.

The present invention overcomes the difficulties set forth above as well as other difficulties generally associated with the aforementioned art references. In particular, both the necessity of cooking the confection to obtain desired physical properties and using excessive water to mix and hydrate one or more ingredients is eliminated, as is the need to overprocess an unpalatable active. In addition, the method and product of the invention are obtained without any need for subsequent dehydration. Heating at high temperatures and mixing to drive off excessive moisture are no longer required. Consequently, the detrimental heat history generally associated with energy-intensive procedures is also eliminated. Separation of the water from the resulting product is avoided and the lowered water activity results in a product having superior physical, storage, and organoleptic properties with reduced microbial growth problems.

SUMMARY OF THE INVENTION

The present invention is directed to a method of making a unique food and drug delivery system, and especially a novel confectionery delivery system, in particular a chewy nougat, by a positive hydrating step and without the need for subsequent dehydrating in order to produce the confectionery mass. The present invention is also directed to the product resulting from the new method of preparation.

In one preferred embodiment, a saccharide-based component is prepared and combined with a hydrated hydrobinding component.

A primary part of the saccharide-based component is a saccharide material such as sucrose, corn syrup solids, polydextrose, and mixtures thereof. A preferred saccharide-based ingredient is polydextrose. Other highly preferred saccharide materials include sucrose and corn syrup solids. Maltodextrin is also highly desirable, as well as mixtures of any of the foregoing. Preferably, the saccharide-based component is substantially dry, that is without added liquid, e.g. water; or oil.

The hydrated hydrobinding component can include a proteinaceous material such as a gelatin, or a food grade gum such as gum arabic, carrageenan, locust bean gum, guar gum, and mixtures thereof. One preferred hydrobinding component includes a mixture of a gelatin and gum arabic. Another preferred hydrobinding ingredient includes a mixture of carrageenan, locust bean gum, and a crosslinking agent. Generally, the gelatin and/or food grade gum imparts viscoelasticity to the confectionery mass, possibly as a result of cross-inking in these materials. (A saccharide ingredient can also be included as part of the hydrobinding component, as for example, a sweetener.)

In another embodiment, the hydrobinding component can also be aerated, preferably in the presence of an aerating agent, prior to or after combining it with the saccharide-based component. Aerating agents include, among other things, egg whites, soy protein, and combinations thereof.

Other ingredients can also be included in conjunction with the hydrobinding component, including oleaginous materials, such as hydrogenated vegetable oils, emulsifiers, and mixtures thereof. These are desirably kept to a minimum, however. Preferably, the hydrobinding component is further employed with a wetting agent or humectant, such as a polyol like glycerin or other commercially available material having similar functionality.

It is further contemplated that one or more active ingredients can be included in the confectionery mass of the present invention. The active ingredients are typically ones which are intended to produce a biological and/or chemical response in the body. The active ingredients can be quite varied, and a non-exhaustive list has been set forth hereinbelow. Preferred actives include antacid materials or bioassimilable sources of calcium, as well as other actives which also have poor organoleptic properties such as foul taste, gritty mouthfeel or bad odor.

In another preferred embodiment of the present invention a nougat mass is prepared which has a chewy consistency and is made with nutritional ingredients so that a health product can be produced. In particular, protein, vegetable and/or fruit components, including dietary fiber, can be added to provide a nutritious food product. If desired, a product having the minimum daily nutritional requirements can be produced. The recommended human adult dietary serving of nutrients is defined by the Consumer Affairs Division of the United States Food and Drug Administration, the publications of which are incorporated herein by reference. In fact a health bar has been prepared which contains the nutritional equivalent of up to five (5) recommended human adult dietary servings of vegetable and/or fruit. Furthermore in this regard, ingredients which have strong olfactory characteristics, e.g., aroma and flavor, can be treated to enhance control of potency before incorporating into a health product prepared in accordance with the invention.

The product resulting from the present invention is unique in part because it requires no cooking and no dehydration by traditional heating at high temperatures to produce. It is substantially free of unbound water and has substantially no phase separation of moisture. The only moisture present is an amount sufficient to bind and functionalize the mass. Thus, the product is fully hydrated, but not excessively hydrated. It is also an intimately mixed confectionery composition having sufficient internal cohesivity to be handled without losing its integrity as a mass.

As herein further described, the product can also be prepared using low or high shear mixing, i.e. with no flash-flow processing required. In other words, the product of the invention may be produced without exposing the components thereof to the high heat and centrifugal forces present in a spinning machine. At the same time, the attributes normally associated with flash-flow processing, e.g. intimate blending of dissimilar ingredients, can still be attained through shear mixing as hereinafter described. It is well known that free moisture in food products can detract from the product. Free moisture has been identified in the art by the use of water activity. In the present invention, the water activity is not greater than about 60% ERH, and is preferably not greater than about 55% ERH.

Another measure of free moisture in foodstuffs is the amount of biological growth within the composition. In the present invention, the biological activity is less than about 100 ppm, preferably less than about 25 ppm, and most preferably less than about 10 ppm.

The present invention also provides the ability to formulate confectionery masses with a significantly reduced fat and calorie content. This result is quite unexpected, since fat has traditionally been used to assist in functionalizing food masses by providing internal lubrication without water.

Other features of the method of the invention include improved processing, intimate mixing and enhanced dispersion of dissimilar ingredients. The final product furthermore exhibits improved content uniformity and improved taste perception qualities. In fact, consumers consistently rate the product of the invention higher than many commercially-prepared similar formulations for such qualities as firmness, flavor, bite, sweetness, chewiness, melt characteristics, stickiness, juiciness, freedom from grit, and aftertaste. Overall, the formulated confectionery delivery system herein described is more palatable than many of the current products available in the art.

For a better understanding of the present invention, together with other and further objects, reference is made to the following description taken in conjunction with the examples, and the scope is set forth in the appended claims.

DETAILED DESCRIPTION OF THE INVENTION

The method for making confectionery-mass delivery systems in accordance with the present invention includes combining a saccharide-based component and a hydrobinding component, the latter component being hydrated sufficiently to provide controlled water delivery to the saccharide-based component and/or other ingredients to fully functionalize the final mass. Controlled water delivery means deliver f water in an amount and at a rate which is sufficient to provide internal viscosity and cohesivity to the saccharide-based component. The word "hydrated" as used in the term hydrated hydrobound component herein means containing sufficient water to provide the requisite controlled water delivery.

The system created by the combination of the present invention is a water-starved system, which means that the system has only enough moisture to bind the ingredients together and provide internal lubricity. Since the ingredients are competing for moisture due to enhanced wettability, there is virtually no free moisture available to separate from the mass.

It may also be extremely desirable to utilize high or low shear mixing, hereinafter set forth, to pre-mix the major components prior to combining with one another. It can also be highly preferred to use the aforesaid high or low shear mixing to mix the final composition containing the saccharide-based component and the hydrobinding component so as to yield the confectionery delivery system herein set forth.

As that term is used herein, high shear mixing refers to relatively intensive mixing action concentrated in a localized area. The high speed impact of mixing mechanisms such as blades or choppers results in shearing action. This in turn creates localized high shear force and a fluidizing effect at the point of contact, which causes particular scale diffusion and disagglomeration and faster mixing in a relatively small area of the entire mixing volume. High shear mixing may also result in increased temperature at the point of impact of the shearing apparatus with the mix, thereby further contributing to the effective mixing action.

High shear mixing should be contrasted with low shear mixing in which the main action of mixing is due to the relative motion of a much larger volume of mix being circulated by the spinning or churning action of a lower impact type mechanism, such as a paddle-blade typically found in a Sigma or Hobart mixer. Whenever high or low shear mixing is utilized to produce the functionalized confectionery mass of the present invention, the resultant product can be referred to as both uncooked and unspun.

As noted, the present invention provides a method and composition for preparing a functionalized confectionery mass without the use of excess water. Functionalization of a confectionery mass means providing the ingredients with sufficient internal cohesivity to be handled without losing its integrity as a mass. In order be handled in the context of functionalization, the mass must also possess internal lubricity which permits inter- and intra-particle movement without loss of cohesiveness. Functionalized food masses have been described as having the consistency of a dough or paste, or as chewy, etc. However, the present invention is not to be limited by any short-hand description of the consistency.

Functionalization of food masses has in the past relied upon the use of significant amounts of added fat, but the present invention enables the artisan to functionalize a confectionery mass without need for added fat if so desired. Functionalization is achieved in the present invention by using certain ingredients, as specified herein. Nonetheless, selected amounts of fat may be added to obtain a confection having desirable perceived texture and/or flavor characteristics.

In the present invention, a hydrated hydrobinding component is used to provide a functionalized hydrobound confectionery mass. A functionalized hydrobound confectionery mass as used herein is a functionalized mass of confectionery ingredients which contains substantially no excessive free moisture or unbound water. A functionalized hydrobound confectionery mass of the present invention does not require dehydration, e.g., by cooking at high temperatures, to remove excess water. The method of the invention, therefore, is substantially more efficient than previously known methods. Less energy costs are expended in the methods herein set forth, while the resulting product is a markedly improved confectionery delivery system.

While applicants do not wish to be bound by theory, it is believed that water is tightly bound to surface polar sites through chemisorption. These sites may include the hydroxyl groups of hydrophilic materials such as proteins, gums, starches, and sugar. Regardless of the actual mechanism, however, this phenomenon is referred to herein as hydrobinding.

A hydrated hydrobinding component is an ingredient which imbibes, delivers and maintains water in an amount sufficient to functionalize the resulting mass. The water which is hydrobound does not separate and become a separate phase. A hydrobinding component cooperates with other ingredients to deliver and maintain water sufficient to functionalize the mass of ingredients.

Thus, a hydrobinding component can be hydrated and then shear mixed with the ingredients (making up the saccharide-based component, hereinafter described) to form a functionalized hydrobound confectionery-mass delivery system. After combining the hydrated hydrobinding component and the additional ingredients, moisture is readily imbibed and disseminated throughout the non-hydrated components and/or ingredients. Unlike prior art methods and confectionery compositions, additional moisture is not required to form a hydrated mixture. Thus, excess water is not present in the resulting mass.

The hydrobinding component and saccharide-based component, acting in concert with one another, capture or bind sufficient moisture to functionalize the total mass. The ingredients capture the moisture by some mechanism as yet unelucidated, possibly physically, chemically, and/or even biologically. Whatever the binding mechanism may be, water is held and made available for absorption by the remainder of the ingredients. The addition of considerable excess water is thus avoided, as is cooking to subsequently drive off the added moisture.

Hydrobinding ingredients useful for the hydrobinding component include, for example, proteinaceous materials known to those skilled in the art, and preferably gelatins of various grades and types. Also preferred are food grade gums such as gum arabic, carrageenan, guar gum, and locust bean gum, and mixtures thereof. A hydrobinding component comprising a mixture of ingredients is desirable in some situations. Highly preferred hydrobinding ingredients include, for example, a mixture of gelatin and gum arabic, or a mixture of carrageenan and locust bean gum with a crosslinking agent, such as potassium citrate or potassium chloride, which induces crosslinking between these materials. These mixed hydrobinding materials are advantageous not only for their hydrobinding capacities, but also because they impart viscoelasticit, to the resulting confectionery. It is possible that crosslinking in these materials contributes to their desirable physical properties. The hydrobinding material can also benefit from inclusion of a wetting agent or humectant such as a polyol known in the art, desirably glycerin, or other functionally similar materials which are commercially available.

The hydrated hydrobinding component will comprise about 0.5–20% of the confectionery delivery system of the invention. Preferably, the hydrobinding component will be within the range of about 5–15%, and even more desirably within the range of about 5–10%. Of the foregoing hydrobinding component, water will comprise about 30–80% thereof, and preferably about 40–70% thereof. The proteinaceous material or the gum(s), or combination thereof, will make up about 0.5 to 60% of the hydrobinding component, and more preferably will be within the range of about 3 to 50%, more desirably about 5 to 20% (unless otherwise set forth, all %s herein are percentages by weight, or weight percent). Another material which may be included as part of the hydrobinding component is a wetting or softening agent, such as a polyol, preferably glycerin, which may be included in amounts equal to about 0–15%, preferably about 0.1–10% of the composition of the invention, even more desirably about 5–10%. The glycerin (or other selected material) typically functions as a humectant, and thereby keeps moisture in the system. The humectant thus further contributes to the successful hydration of the hydrobinding component, and ultimately all components of the final confectionery mass.

The hydrobinding component, e.g., the gelatin and/or gum, can also be aerated, preferably in the presence of an aerating agent, before or after being combined with the other processed ingredients. Preferred aerating agents include egg whites and soy protein. Aerating agents are desirably added in amounts within the range of about 0–5%, more desirably 0.1–3%.

It is also within the scope of the invention that ingredients which are used in the hydrobinding component, and particularly the dry ingredients thereof, may instead be included, at least in part, with the saccharide-based component. Thus, in another embodiment, gelatins and food grade gums such as gum arabic, carrageenan, guar gum, locust bean gum, etc., can be used to prepare the saccharide-based component, e.g., by being included in the feedstock used to prepare that component.

The invention also employs a saccharide-based material as another major component (the hydrobinding component material being the first major component). The saccharide-based component can include any of a large variety of saccharide materials, such as small sugars, e.g., dextrose, sucrose, fructose, etc., and larger saccharides such as corn syrup solids and polydextrose, as well as mixtures of two or more of these materials.

Corn syrup solids are highly preferred for use as the saccharide-based material in the composition of the invention. Corn syrup solids arc commonly known as maltodextrins. Maltodextrins are composed of water soluble glucose polymers obtained from the reaction of the starch with acid or enzymes in the presence of water. The hydrolysis reaction produces a carbohydrate mixture of saccharides having a controllable dextrose equivalence (D.E.), commonly a D.E. of less than 20. When the hydrolysis is permitted to proceed to an extent sufficient to produce a D.E. of greater than 20, the FDA calls the resulting materials corn syrup solids.

Polydextrose is a non-sucrose, essentially non-nutritive, carbohydrate substitute. It can be prepared from polymerization of glucose in the presence of polycarboxylic acid catalysts and polyols. Generally, polydextrose is known to be commercially available in three forms: Polydextrose A and Polydextrose K, which are powdered solids, and Polydextrose N supplied as a 70% solution. Each of these products can also contain some low molecular weight components, such as glucose, sorbitol, and oligomers. Sugars can also be used as saccharide-based materials according to the invention. Sugars are those substances which are based on simple crystalline mono- and di-saccharide structures, i.e., based on $C_5$ (pentose) and $C_6$ (hexose) sugar structures. Sugars include dextrose, sucrose, fructose, lactose, maltose, etc., and sugar alcohols such as sorbitol, mannitol, maltitol, etc. Other saccharide material can include tri-, tetra- and oligosaccharides.

Typically, the foregoing saccharide-based component can comprise about 30–99.5% of the confectionery delivery system according to the embodiments herein set forth. Preferably, there will be about 40–75% of this component present, and even more desirably about 50–70% present. In addition, those skilled in the art may discover a higher or lower percentage of the saccharide-based component, or other ingredients herein set forth, will produce a suitable final product, depending upon the final characteristics, eg. texture, mouth feel, product consistency, etc., which are desired. A highly preferred saccharide-based component will comprise a mixture of corn syrup solids and sucrose in a ratio of approximately 50/50 or 40/60.

Preferably, the saccharide-based component is substantially dry, i.e. is in non-liquid form and is without added moisture, e.g. water. It has now been found that while materials such as sugar alcohols and acqueous-based saccharide formulations may be utilized herein, it is best that their presence is at least kept to a minimum in most embodiments. The addition of too much liquid-based saccharide component may cause the final confectionery mass to be too gooey, sticky, tacky and/or gummy, and therefore highly unsuitable for processing, handling, and consuming.

Other materials which can be incorporated into the confectionery mass of the invention, to enhance its appearance, taste, texture, and other perceptions of the consumer, include, for example, flavors, sweeteners, colorants, surfactants or emulsifiers, and fats or oils. Any one or a combination of more than one of the foregoing may comprise from about 0–20% of the confectionery mass, and more desirably be within the range of about 5–10% or even up to 15% of the comestible mass.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime, and grapefruit, as well as fruit essences including, for example, apple, pear, peach, grape, strawberry, raspberry, cherry, plum, pineapple, apricot, or other fruit flavors.

Other useful flavorings include, for example, aldehydes and esters such as benzaldehyde (cherry, almond), citralm, i.e., alphacitral (lemon, lime), neural, i.e., betacitral (lemon, lime) decanal (orange, lemon), aldehyde $C_8$ (citrus fruits), aldehyde $C_9$ (citrus fruits), aldehyde $C_{12}$ (citrus fruits), tolyl aldehyde (cherry, almond), 2,6-dimethyloctanal (green fruit), and 2-dodecenal (citrus, mandarin), mixtures thereof, and the like. Other flavorings may include whole and partial fruits and nuts, peanut butter, candy bits, chocolate chips, bran flakes, etc.

Sweeteners may also be added to the confectionery delivery system of the invention. These are typically included to enhance the flavor and impart a palatable sweetness to the confectionery mass. The sweeteners may be chosen from the following non-limiting list and may be added in addition to the saccharide-based component materials: glucose (corn syrup), dextrose, invert sugar, fructose, and mixtures thereof saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used. The sweeteners are added in amounts equal to about 0–10% of the composition, and preferably about 0.1–5%.

Surfactants or emulsifiers may also be included in the composition of the invention. These may be any food grade emulsifying material, for example, lecithin or other phospholipid material, monoglycerides and/or diglycerides, and mixtures thereof in amounts of from about 0–3%, more desirably about 0.1–1%.

Fats may also be included in the composition, and these can include partially or entirely unsaturated fats such as palm oil and cocoa butter. Hard fats having melting points above body temperature (37.6° C.), and soft fats having a melting point of about or below body temperature, can be used alone or in combination. The texture and mouth feel of the resulting confection can be influenced by selecting the types and amounts of fats included in the saccharide-based component. Fats marketed under such trade names as Durem and Paramount have been found to be useful. Those skilled in the art will find that fats are optional as part of the composition of the invention, and may be eliminated altogether if so desired. Thus, fats will comprise about 0–10% of the product herein set forth, preferably less than about 7%, and even more preferably less than about 5%. Fats are highly preferred over oils because of their solid nature which makes them easier to blend with the other ingredients of the invention, e.g. the saccharide-based component.

Additional materials which can be incorporated into the composition of the invention include, for example, biologically active ingredients such as medicinal substances, e.g. drugs, pharmaceuticals and antacids. These are referred to herein as active ingredients or bioaffecting agents. Active ingredients may make up from about 0–50% of the product of the invention, desirably from about 0.1–50%, and may be more depending upon the needs and abilities of those skilled in the art. It is preferred, however, to include at least about 20%, more preferably about 25%, and even more desirably up to about 40% of one or more active ingredients in the compositions set forth herein.

As active ingredients, the medicinal substances capable of incorporation and delivery according to the invention are extremely varied (those skilled in the art may conceive of others than those herein described, and these are certainly within the scope of the invention). An exemplary, non-limiting list of such medicinal substances includes: antitussives, antihistamines, decongestants, alkaloids, mineral supplements, laxatives, vitamins, e.g. vitamin D3, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparation, diuretics, antispasmodics, uterine relaxants, mineral and nutritional additives, antiobesity drugs, anabolic drugs, erythropoietic drugs, antiasthmatics, cough suppressants, cold remedies, mucolytics, anti-uricemic drugs, nicotine and mixtures thereof.

Analgesics include, for example, aspirin, acetaminophen, and acetaminophen plus caffeine.

Other preferred drugs for other preferred active ingredients for use in the present invention include, for example, antidiarrheals such as IMMODIUM AD®, antihistamines, antitussives, decongestants, vitamins, and breath fresheners. Also contemplated for use herein are anxiolytics such as XANAX®; antipsychotics such as clozaril and HALDOL®; non-steroidal anti-inflammatories (NSAIDs) such as VOLTAREN® and LODINE®; antihistamines such as SELDANE®, HISMANAL®, RELAFEN®, and TAVIST®; antiemetics such as KYTRIL® and CESAMET®; bronchodilators such as BENTOLIN®, PROVENTIL®; antidepressants such as PROZAC®, ZOLOFT®, and PAXIL®; antimigraines such as IMIGRAN®, ACE-inhibitors such as Vasotec, Capoten and Zestril; anti-Alzheimer's agents, such as NICERGOLINE; and $Ca^H$-Antagonists such as PROCARDIA®, ADALAT®, and CALAN®.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Other active ingredients include antiplaque medicaments and medicaments for veterinary use.

Especially preferred active ingredients contemplated for use in the present invention are antacids, $H_2$-antagonists, and analgesics. For example, antacid dosages can be prepared using the ingredients calcium carbonate ($CaCO_3$), either alone or in combination with magnesium hydroxide, and/or aluminum hydroxide. Moreover, antacids can be used in combination with $H_2$-antagonists.

Active antacid ingredients include, but are not limited to, aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum monobasic or dibasic calcium phosphate, tricalcium phosphate, potassium bicarbonate, sodium tartrate, sodium bicarbonate, magnesium aluminosilicates, and tartaric acids and salts.

Calcium supplement products can also be prepared by incorporation of a bioassimilable calcium source in the comestible delivery system confectionery of the invention. Typically, calcium supplements require a larger addition of calcium than do antacids. Preferably, the calcium source is calcium carbonate, but other sources of calcium capable of absorption or bioassimilation can be employed, including finely divided bone meal or oyster shell materials and the like. The calcium-containing material is preferably very finely divided so as not to impart any unnecessary chalkiness or other unpalatable characteristic to the confection. Moreover, the calcium is preferably provided in substantially dry form; that is, is not pre-treated or pre-coated in a separate step with a liquid such as water or an oleaginous substance, such as wax or oil. Applicants have discovered that "dry" calcium can be more intimately and easily dispersed throughout the resultant confectionery mass. Finely ground calcium materials are commercially available, e.g., from Specialty Minerals, for use either in the antacid products or calcium supplement products. In one preferred embodiment of the invention, a calcium supplement product is prepared which incorporates 500 mg. Of bioassimable calcium, along with 200 I.U.'s of vitamin D3 into a single dosage form of the final product, which represents 50% of the RDA of those nutrients.

In an especially preferred embodiment of the invention, a calcium source may be combined with a magnesium source to yield a mineral supplement "active" included in various embodiments of the chewy nougat formulation. Magnesium has been recognized as an essential element which aids in metabolism. Magnesium also aids in the absorption of calcium, and is therefore highly desirable as an additional component of a chewable, nougat calcium supplement formulation. Any bioassimilable magnesium source may be utilized. Non-limiting examples include those selected from the group consisting of magnesiums oxide, hydroxide, phosphate, carbonate and lactate, for example. Of these, magnesiums oxide, carbonate and lactate are more preferred. Magnesium lactate is desirable because it is highly stable for extended periods, and its inclusion in a chewy supplement imparts very little or and color, flavor, sweetness or textural off-notes thereto. These attributes may be particularly important from a commercial point of view.

An especially preferred dietary supplement therefore includes about 500 mg. of bioassimable calcium, about 40 mg. magnesium, and about 200 I.U.'s of Vitamin D3 into a single dosage form. This represents 50% of the RDA for these nutrients. More or less of the foregoing nutrients may be added, depending upon the particular needs of the skilled artisan. For example, a proportional scale-up or down of the foregoing substituents could be utilized to yield a formulation having, for example, 75%, 100% or even 25% of the foregoing nutrients.

It is certainly within the scope of the invention to include in a chewy nougat dietary supplement from about 20–40% of a calcium source, about 0–5% of Vitamin D3 and about 0–50% of a magnesium source. More preferably, at least about 23–40% of a calcium source, about 1–5% of Vitamin D3, and about 1–20% of a magnesium source may be included in the chewy nougat dietary supplement heretofore described.

The products according to the various embodiments of the invention are tasty and sweet chewy nougat confectioneries, with a smooth texture and consistency, with no grit or chalkiness. These products are well hydrated, and yet evidence no phase separation of moisture upon extended periods of storage. They are therefore extremely suitable for marketing on a large commercial scale.

One of the advantages of the present invention is that a large proportion of the product can be displaced by a bulky material, such as for example calcium sources. For example, it is preferred that up to about 25–35% or even more of the total weight of the resulting product can be an added bioassimilable calcium source, without imparting undesirable taste or texture to the product. In fact, the product according to several embodiments of the invention exhibits improved taste and texture characteristics as compared with similar commercially-available products. "Improved" means that individual consumers rate the product overall to be superior when such characteristics as firmness, flavor, bite, sweetness, chewiness, melt characteristics, stickiness, juiciness, freedom from grit, and aftertaste are analyzed. Thus, while the product of the invention may contain as much as one-quarter or even more of an unpleasant active such as calcium, it still exhibits a smooth, nougat texture and taste very similar to, or virtually indistinguishable from that of a confectionery such as a tootsie roll or Charleston chew. (Of course, useful comestible delivery systems can also be produced wherein as little as only a trace amount of the total weight of the product is a deliverable active ingredient.)

In addition, the product of the invention according to its various embodiments preferably has the attributes of a shearform matrix, as hereinafter described.

Another active component which can be included in products made in accordance with the present invention is a nutritional component. A nutritional component can include ingredients such as vitamins and minerals required to maintain good health. A health bar product has been prepared in accordance with the present invention which includes a dry residue of whole vegetables and/or fruits. In fact, a health bar product has been made which includes the nutritional equivalent of up to five (5) times the U.S. recommended human adult dietary serving of vegetables and/or fruit by incorporation of the dry residue of such fruits and vegetables. Other bulky materials can also be included, e.g., dietary fiber, in the confectionery delivery system of the invention.

A preferred embodiment of the nutritional form of the product contemplates treating ingredients having strong olfactory characteristics, e.g., flavor and aroma, to reduce such characteristics. For example, dry residue of spinach and broccoli have been treated by heating in the presence of yogurt powder and a small amount of moisture to drive off strong aroma and flavor notes. This technique conditions such ingredients for incorporation in a health product without detracting from the overall smell and taste of the product. It has been found that the above technique is particularly effective for preparing a nutritional health bar product.

Another nutritional component can include protein from animal and/or vegetable sources (to be distinguished from the proteinaceous material utilized in the hydrobinding component), either alone or together with soluble and/or insoluble dietary fiber, as well as one or more vitamins and minerals.

Also to be included as active ingredients include such naturally-derived products as botanical substance extracts, which may include certain derivatives of plants and herbs, as for example, bark, seeds, stem, leaves, roots, berries and flowers. The botanical extracts would much desirably be those which are recognized for their natraceutical properties. Non-limiting examples of these botanical substance extracts could include ginseng, ginkoba, gingko siloba, St. John's wort, and the like. One source of these materials may be found under the brand name STAND-EX™ from Bio-Botanica, Inc., including Lipo Chemicals.

In one desirable embodiment of the invention, the confectionery composition of the invention includes a saccharide-based component, a hydrobinding component, and at least one member selected from the group consisting of vitamins A, B complex (including B1, B2, B6, B12 and biotin), C, D and E.

The product resulting from the present invention is unique because it requires no cooking and no dehydration by traditional heating at high temperatures to produce, and has substantially no phase separation of moisture. The only moisture present is found therein in an amount sufficient to functionalized the mass. Thus, the product can be prepared without cooking.

As heretofore set forth, the chewy confectionery composition herein set forth can also contain one or more other active substances which until now could not be easily administered via a chewable delivery system because of their relatively poor organoleptic properties. These biological and chemical substances are fairly unpleasant looking, tasting or smelling, have a disagreeable mouthfeel, or are otherwise difficult to swallow. Chewing would normally only exacerbate the unpleasantness. The unique confectionery system herein provided effectively taste masks many or all of these substances, and thereby functions as a unique delivery system for these actives. Thus, it is clearly within the scope of the invention to provide a confectionery system containing all types of "unpleasant" actives which can be easily masticated and swallowed like any nougat-type candy. These compositions are sweet-tasting and therefore are easily administered. At the same time, the heretofore described components constituting these formulations effectively taste-mask the bitterness and bad taste associated with these myriad drugs, food substances and nutraceuticals.

One such active as part of the invention is caffeine. The drug itself has long. been recognized as enhancing alertness. It can be provided as a nutritional supplement for those who wish to remain awake and cognizant for extended periods. Unfortunately, caffeine is an extremely bitter tasting white chemical compound, and therefore is not a likely candidate for inclusion in a chewy confectionery formulation. As part of the composition of the invention, however, it is rendered into an extremely delicious, chewable form with excellent mouthfeel. The chewy confectionery herein described thus functions as a delivery system for the caffeine, as well as for other active substances. When included, a dosage of caffeine within the range of about 0.1 to 500 mg is recommended. Preferably, a single serving should contain about 10 to 150 mg of caffeine. It is especially desirable to include about 25 to 100 mg. in a single dose. On a weight basis, any caffeine will typically make up about 0.1 to 5% of the final composition of the invention, and more desirably be within the range of about 0.5 to 2%. These amounts can vary, depending upon the desires of the particular skilled artisan.

The confectionery products according to the various embodiments heretofore described are unique, in part because they require no dehydration to produce, i.e., the product can be prepared without cooking. Moreover, there is substantially no separation of moisture in the resulting product. The only moisture present is an amount sufficient to functionalize the mass. No excess water is thus necessary to prepare the product or is present in the final formulation.

The hydrobound system of the present invention is a mass which has been hydrated by adding moisture to provide hydrocolloidal stability, but which does not have measurable free water, e.g., syneresis is substantially halted. Syneresis refers to as the phenomenon of separation of water from a mass of material as a distinct phase. When the moisture is so minimal in a mass or sufficiently bound to other components in the mass that phase separation does not occur, syneresis is stopped or halted. When syneresis occurs, free water is available within the system. Free water is generally unwanted in confectionery products of the type disclosed herein because of product deterioration and micro-organic growth. A correlation between free water and water activity has been made as a measure of product stability. Many properties of foods are affected by the content and nature of water which they contain. Water participates in mass transfer and chemical reactions where it assumes a major role in determining physical and chemical content of foods. The production of a new food must almost inevitably confront the nature of water if the final product is to be stabilized with regard to nutritional content, microbial growth, and other factors.

A well-known method for characterizing the presence of water is by water activity. Water activity is measured as the ratio between the vapor pressure of water in an enclosed chamber containing a food and the saturation vapor pressure of water at the temperature. Water activity indicates the degree to which water is bound and, subsequently, available to act as a solvent or participate in destructive chemical and microbiological reactions.

When the water activity is low, water is unavailable because it is tightly bound to surface polar sites through chemisorption. Water activity is defined as:

$$a_w = \frac{p}{P_0}$$

where $a_w$ is water activity, p is the partial pressure of water above the sample, and $P_0$ is the vapor pressure of pure water at the same temperature (must be specified). Another defi nition of water activity which is more thermodynamically appropriate is $$a_w = \frac{P_{eq}}{P_0}$$

where $P_{eq}$ is the partial vapor pressure of water in equilibrium with the solution and $P_0$ is the vapor pressure of pure water at the same temperature and pressure as the solution. When a solute is added to water, water molecules are displaced by solute molecules and the ratio of the vapor pressures or $a_w$ is altered. Entropy is also lowered as solute molecules become oriented to water molecules. As a result, water molecules are not as free to escape from the liquid phase and the vapor pressure is therefore decreased. This change is governed by Raoult's law, which states that the decrease in vapor pressure of a solution is equal to the mole. fraction of its solute. Similarly the ratio of vapor pressures ($a_w$) is governed by the number of moles of solute ($n_1$) and solvent ($n_2$):

$$a_w = \frac{P}{P_0} = \frac{n_1}{n_1 + n_2}$$

Different solutes tie up or bind water to varying degrees depending on the nature of the solute, such as its level of dissociation, extent and nature of intramolecular binding, solubility and chemical components.

Further, a portion of total water content present in foods is strongly bound to specific sites on the chemicals that comprise the foodstuff. These sites may include the hydroxyl groups of polysaccharides, the carboxyl, amino groups of proteins, and other polar sites that may hold water by hydrogen bonding or other strong chemical bonds. In addition to strongly bound water molecules, some of the water in foods is usually bound less firmly but is still not available as a solvent for various water-soluble food component. Thus, water activity is low when water is tightly bound to surface polar sites through chemisorption. The sites can include hydroxyl groups of hydrophilic material which are effective in controlling water activity.

In the present invention water activity is significantly lower than water activity of similar products found in the candy bar industry. For example, candy bars usually have a water activity of 62%–68% equilibrium relative humidity (ERH). The confectionery product of the invention, however, has at most only about a 60% ERH, and is preferably not greater than about 55% ERH.

Another measure of free water in foodstuffs can be provided by the amount of biological growth within the composition. In the present invention, the biological activity is less than about 100 ppm, preferably less than about 25 ppm, and most preferably less than 10 ppm.

Another distinctive feature of the present invention is the ability to reduce fat and calories in confectionery products. As a result of the present invention, a confectionery nougat product can be made which has little or no fat content. This product qualifies under industry standards to be referred to as Reduced Fat (which means the fat content is reduced by at least 1/3) and as Low Fat (which means the fat content is reduced by at least 50%).

It has now been further discovered that at least some of the confectionery embodiments of the invention can be advantageously provided in the form of a shearform matrix, that is, as a matrix in which all components are intimately combined and randomly dispersed throughout the entire confectionery. Shearform matrix materials are known to exhibit significantly enhanced wettability because of a randomized structure which until now has resulted primarily from flash-flow processing as described in U.S. Pat. No. 5,587,198, in which processing is undertaken in a centrifugal machine in which material is exposed to high heat. As applicants have now discovered, a shearform matrix can now also be obtained from high and/or low shear mixing.

It is therefore particularly preferred to use the aforementioned low and high shear mixing processes to prepare the product of the invention according to its various embodiments. In this way, the added time and expense associated with other methods of processing can be avoided. The same qualities associated with the final product which can be attained with flash-flow processing can now also advantageously be attained through the use of shear mixing methods.

As noted hereinabove, the hydrobinding component is a component which imbibes, delivers and maintains water in an amount sufficient to functionalize the resulting mass. The water which is hydrobound does not separate and become a separate phase. Accordingly, the hydrobinding component cooperates with other ingredients to deliver and maintain water sufficient to functionalize the mass of ingredients, including those ingredients which have been subjected to flash-flow processing.

Thus, the hydrobinding component can be hydrated and then high and/or low shear mixed with the saccharide-based component (the latter also being prepared as a result of low or high-shear mixing) in order to form a fully functionalized hydrobound confectionery mass. After combining the hydrated hydrobinding component and the saccharide-based component, moisture is readily imbibed and disseminated throughout the non-hydrated components and/or ingredients. Again, unlike prior art methods and confectionery compositions, additional moisture is not required to form a hydrated mixture. Thus, excess water is not present in the resulting mass.

Other materials, as heretofore outlined, can be incorporated into the saccharide-based component or the hydrobinding component to promote the shearform matrix-like attributes and include, for example, flavors, sweeteners, colorants, surfactants or emulsifiers, and oleaginous materials such as fats and oils. Any of the adjunct materials described herein above can be included in the preparation of a suitable product with shearform matrix characteristics.

As heretofore noted, it has now been discovered that the same attributes in the final product of prior art formulations, e.g. intimate mixing, can now also be attained by shear mixing, such as high or low shear mixing, of the saccharide-based component and other materials such as actives, prior to combining with the hydrated hydrobinding component, e.g. gum or gelatin, again using shear mixing. In some instances, a combination of flash-flow process and shear mixing may be utilized to produce the product of the invention. For example, certain ingredients making up the saccharide-based component may be subjected to flash-flow procedures (such as pre-flash-flow processing) in order to combine them. However, any flash-flow processing is best kept to a minimum. Once combined, the saccharide-based component can then be shear mixed with the hydrated hydrobinding component to produce the food and/or drug delivery system of the invention.

It has been further discovered that hydrating the hydrobinding component before mixing with the saccharide-based component is a much more preferred method of combining ingredients than is simply random mixing, or a method of combining in which all components are immediately dumped together in a shear mixing apparatus. Without being bound by any particular theory, it seems that by hydrating the hydrobinding component separately, and then combining that component with the saccharide-based component, the necessary hydration and functionalization of the resultant mass is much more effectively attained.

An especially preferred high-shear mixer for use with the invention is known as a Littleford FKM 1200. This device provides high shear mixing by proximal shearing blades which are at right angles to one another. The shearing blades consist of "plowers " and choppers, both of which are utilized for high shear mixing action. While not wishing to be bound by any particular theory, it is believed that high shear action provides both mixing and heating at the localized points of blade contact with the mix ingredients, thereby resulting in excellent dispersibility without the undesired effects of lumping etc. Other high shear mixers (with one or more mixing blades), currently available or yet to be developed, are also contemplated by the method of the invention.

If desired, the high shear mixer can be further equipped with a jacket heater to provide the benefits of additional warming (but not cooking). A preferred temperature range for warming is therefore from about 30 degrees C. to about 60 degrees C., more desirably within the range of about 30 degrees to about 45 degrees C.

A preferred procedure for high shear mixing the composition of the invention is as follows: The jacket heater on the high shear mixer is first activated and allowed to warm to a temperature of about 40 degrees C. Next, the saccharide-based component and other dry ingredients, e.g. calcium carbonate, are fed through the open hopper and allowed to mix using the plowers. For an 18 pound mixture, for example, the device is first run for about 2 minutes. Any added fat, along with emulsifiers, and the liquid-based hydrobinding component (together with any flavorings, sweeteners and coloring) are then fed into the mixer, and the choppers or high shear blades are activated to further complete the mixing. During this time, the jacket temperature may be increased to within the range of about 50–60 degrees C., preferably about 58–60 degrees to assist in the mixing, especially if fat is present in the mixture. The mixer is then run for about 5–10 minutes more, perhaps longer, to complete the mixing of the saccharide-based component and the hydrobinding component. Once mixing is complete, the entire matrix is then emptied into an appropriate container for slicing, sorting and shipping etc., e.g. is extruded and cut into dosage size pieces.

In certain preferred embodiments , the use of a low shear mixing apparatus can also provide the product of the invention. Of these, a Sigma mixer and/or Hobart industrial paddle mixer may be suitable. In one preferred embodiment, the dry ingredients (saccharide-based component and any additional materials, e.g. one or more actives) are mixed in a Sigma mixer until a good consistency is obtained. Separately, the liquid ingredients (hydrobinding components) are mixed in a Hobart mixer, and then added to the Sigma mixer with the dry ingredients. The whole mixture is then run in the Sigma mixer for about 3 minutes. Variations of the foregoing process are certainly within the scope of the invention, depending upon the characteristics of the individual ingredients, and the attributes desired within the final product. The goal is to achieve enhanced hydration and intimate mixing of all ingredients so that the final confectionery is a chewy, nougat-type confectionery with a good mouthfeel in which any unpleasant smell or taste perceptions which may be associated with the "raw" ingredients is effectively masked.

Another method of formulating the product of the invention utilizes both high- and low-shear mixing apparatus. Dry ingredients such as corn syrup solids and sucrose (polysaccharide component) are first mixed together with other dry ingredients, e.g. calcium carbonate, as well as any optional fat-based component and any emulsifier(s), in a high shear mixer, preferably a Littleford FKM 1200, according to the procedure described above (plowers first, followed by shearing blades for about 5–10 minutes). Next, in a low shear mixer (e.g. Hamilton) the liquid ingredients, i.e., the hydrobinding component along with any optional, additional sweeteners, flavorings, colors and if desired, vitamin D3 formulation dissolved in corn syrup, are mixed together for a few minutes. This resulting mixture is then added to the dry mix (which has now been transferred from the high shear mixer to another low shear mixer, e.g. Guittard). All ingredients are then mixed in this second low shear mixer for a few more minutes (~3 minutes), with the resulting mass then sent through an extruder for final processing such as slicing, sorting and shipping, etc.

In still another embodiment of the method of the invention, the saccharide-based component along with the calcium carbonate and vitamin D3 are first mixed together in the high shear mixer. The resulting formulation is then added to an extruder together with the liquid ingredients (hydrobinding component) for final mixing, and extrusion. The extruder would of course be of the type known in the art which is adapted to receive liquid components.

Through the use of or shear mixing the need to cook the confectionery product of the present invention is thus eliminated. Also, the need to spin the material can also be preferably eliminated.

For a better understanding of the present invention, together with other and further objects, the following examples and tables are provided to illustrate the unique methods of making a confectionery mass and products resulting therefrom. Unless otherwise specified, percentages of components in the compositions are given as percentage by weight (wt %). Also, unless otherwise indicated, all materials were obtained from commercial suppliers.

The following examples sense to illustrate various embodiments of the invention, but in no way should they be construed as limiting the scope thereof.

EXAMPLE 1

A series of confectionery-type masses was prepared according to the invention, for the delivery of a bioassimilable calcium source, in this case dry powdered calcium carbonate. The hydrobinding material was selected to be a mixture of medium weight gelatin (250 Bloom) and gum arabic. The saccharide-based material was selected to be sucrose (6X) or a mixture of sucrose and corn syrup solids. The components and the preparation conditions for these batches are given below in Table 1.

In this series of batches, the gelatin and gum arabic were premixed with glycerin. Then a controlled amount of water was added thereto, along with flavoring and color. The calcium carbonate and the saccharide-based material (corn syrup solids and sucrose) were added to a Littleford FKM-1200 high shear mixer. The mixer was then operated for 2 minutes using the plowers only. The premixed fat/emulsifier/sorbitan mixture was added to the mixer. The hydrated hydrobinding material above (gelatin et al.) was also added, and the resulting mass was mixed with an FKM-1200 high shear mixer for approximately 5–10 minutes.

TABLE 1

| MATERIAL (wt %) | BATCH 1A | BATCH 1B | BATCH 1C | BATCH 1D | BATCH 1E |
|---|---|---|---|---|---|
| Gelatin | 1–5% | —, | —> | —> | —> |
| Gum Arabic | 0.1–1% | —, | —> | —> | —> |
| Flavoring | 0.1–1% | —, | —> | —> | —> |
| Water | 5–10% | —, | —> | —> | —> |
| Glycerin (99%) | 0.1–3% | —, | —> | —> | —> |
| Color | 0.1–0.5% | —, | —> | —> | —> |
| Calcium Carbonate | 28.57% | —, | —> | —> | —> |
| Sugar 6X | 25–40% | 25–40 | 60–70 | 25–40 | 25–40 |
| Corn Syrup Solids | 25–40% | 25–40 | — | 25–40 | 25–40 |
| Fat Solids | 3–10% | —, | —> | —> | —> |
| Lecithin | 0.1–1% | —, | —> | —> | —> |
| Sorbitan | 0.1–1% | —, | —> | —> | —> |
| Kettle Tamp | 43° C. | 40° C. | 40° C. | 35° C. | 4° C. |
| Dry Powder Temp | 39° C. | 36° C. | 40° C. | 32° C. | 40° C. |
| Fat System Temp | 74° C. | 55° C. | 54° C. | 56° C. | 86° C. |
| Binder Temp | 45° C. | 44° C. | 44° C. | 45° C. | 48° C. |
| Final Product Temp | 39° C. | 50° C. | 40° C. | 42° C. | 43° C. |
| Maxing Time (Min) | 5 | 5 | 5 | 5 | 5 |
| Mixing Speed (%) | 40 | 40 | 40 | 60 | 60 |

All of these batches yielded products which were extruded and cut into pieces calculated to deliver about 500 mg of bioassimilable calcium. The products varied in the degree of tackiness to touch, but all were chewy with a nougat consistency, much like that of a Tootsie Roll, with more than acceptable mouthfeel with at most only a minor amount of chalky texture on chewing. Thus, a nougat product quite acceptable to consumers is produced 1) without driving off excess water, 2) without cooking the material and 3) without spinning the material.

EXAMPLE 2

A nougat composition was prepared without cooking or removal of water. The ingredients set forth in Table 2-A were mixed using a high shear mixer for 5 min at 40–50 cycles/min.

TABLE 2-A

| Ingredient | Percent of Composition |
|---|---|
| Calcium Carbonate | 28.75 wt % |
| Powdered Sugar | 30–40 wt % |
| Corn Syrup Solids, DE 36 | 30–40 wt % |
| Fat Solids | 3–8 wt % |
| Emulsifiers | 0.1–1 wt % |
| TOTAL | 100 wt % |

This mixed composition was then mixed with colors and flavors in a Sigma mixer, again for 5 min at 40–50 cycles/min.

In a separate vessel, glycerin and a vegetable gum were mixed and stirred to smoothness. Water was added, and again the mixture was stirred to smoothness. Gelatin was then added along with flavoring and coloring, and the mixture was stirred for about 1 minute to thicken. This mixture was then warmed to about 50° C. in a microwave oven for about 30–45 sec. The warmed mixture was added to the primary mixture, and stirred with the Sigma mixer for about 5 min at 40–50 cycles/min. The final product composition is presented in Table 2-B.

TABLE 2-B

| Ingredient | Percent of Composition |
|---|---|
| Primary Mixture | 80–90 wt % |
| Flavoring | 0.1–1 wt % |
| Coloring | 0.1–1 wt % |
| Glycerin | 0.5–3 wt % |
| Vegetable Gum | 0.1–1 wt % |
| Water | 5–10 wt % |
| Gelatin | 1–5 wt % |
| TOTAL | 100 wt % |

The resulting mass was removed from the mixer, and rolled to the desired thickness, e.g., about 3 cm. This product was completely homogeneous, and had a chewy texture and was extremely tasty.

EXAMPLE 3

The primary mixture prepared according to the method described in Example 1 was used to make a gelatin-free confection product suitable for use as a calcium supplement. The primary mixture, together with flavorant, colorant, and an artificial sweetener, were mixed together in a kettle for 5 min. Potassium citrate was then dissolved in water with warming to ~85 degrees C. The hot solution was immediately added to a mixture of locust bean gum, carrageenan, and glycerin in a beaker and mixed, to provide a warm paste. This paste was then added to the pre-mixed primary mixture, and mixed for about 5 min. The final temperature of the resulting nougat was ~50 degrees C. The amounts of the ingredients in this chewy nougat confection are given in Table 3.

TABLE 3

| Ingredient | Percent of Composition |
|---|---|
| Primary Mixture | 85–95 wt % |
| Flavoring | 1–3 wt % |
| Coloring | 0.001 wt % |
| Aspartame | 0.009 wt % |
| Locust Bean Gum | 0.1–1 wt % |
| Carrageenan | 0.1–1 wt % |
| Glycerin | 2–7 wt % |
| Potassium Citrate | 0.1–1 wt % |
| Potable Water | 2–7 wt % |
| TOTAL | 100 wt % |

This pleasant-tasting and chewy gelatin-free nougat material was cut into approximately 5.3 g pieces, each of which provided 500 mg of calcium.

EXAMPLE 4

An additional chewy nougat product was made according to the method set forth in Example 1 which delivered 500 mg of calcium and 200 I.U.'s of vitamin D3 in chocolate, mint and cherry flavors in a 5.3 gram piece according to Table 2 below as follows:

TABLE 4

| Ingredient | Percent of Composition |
|---|---|
| Calcium Carbonate | 23.7% |
| Corn Syrup Solids | 18.1–27.1% |
| 6X Powdered Sugar | 26.6–35.6% |

TABLE 4-continued

| Ingredient | Percent of Composition |
|---|---|
| Additional Corn Syrup Solids | 2.6–3.0% |
| Fat Solids (Paramount B) | 5.9% |
| Lecithin 3F UB | 0.35% |
| Emulsifier (DurEm 117) | 0.25% |
| Sorbitan Stearate (Sorbitan 60K) | 0.25% |
| Vitamin D3* | 2% |
| Glycerin | 3.0% |
| Gum Arabic | 0.4% |
| Gelatin (250 Bloom) | |
| Water | 6–7% |
| Flavorings** | 0.64–1.2% |
| Coloring | 0.01% |
| Acesulfame K (Hoechst) | 0.10% |

*Vitamin D3 was dissolved in a small amount of corn syrup and added with teh liquid components.
**Flavorings included the following: Peppermint, Spearmint, Vanilla, Cream, Chocolate, Cocoa Powder and Cherry.

Consumer Taste Preferences

A mint-flavored chewy nougat formulation according to the foregoing embodiment was compared with three leading commercially-available (store bought) calcium supplement preparations in a random taste test. 100 consumers between the ages of 30–70 were chosen to participate and evaluate a total of four products according to the following criteria on a scale of 1–9: bite, firmness, flavor, sweetness, chewiness, melt, stickiness, juiciness, grit, aftertaste and coolness (the higher the score, the more positively the consumer judged each attribute). Each consumer was given an identical bite-size serving of each one of the four products in the same order (with crackers and a sip of water in between each serving). Consumers were not told the source or identity of the products they were evaluating, other than that each was a calcium supplement. Results are indicated below:

| PRODUCT | PRODUCT A | PRODUCT B | PRODUCT C | INVENTION |
|---|---|---|---|---|
| BITE | 5.95 | 3.78 | 4.11 | 6.49 |
| FIRM | 6.11 | 4.24 | 4.49 | 6.43 |
| FLAVOR | 5.65 | 4.43 | 4.81 | 6.57 |
| SWEET | 5.89 | 4.65 | 5.49 | 6.35 |
| CREW | 6.41 | 3.78 | 4.00 | 5.81 |
| MELT | 5.62 | 4.65 | 4.43 | 5.86 |
| STICK | 5.22 | 4.95 | 4.81 | 4.81 |
| JUICINESS | 5.19 | 4.57 | 4.35 | 5.81 |
| GRIT | 6.27 | 3.59 | 3.22 | 5.84 |

| PRODUCT | AFTERTASTE | COOLNESS |
|---|---|---|
| Product A | 6.49 | 6.38 |
| Product B | 4.89 | 4.97 |
| Product C | 4.92 | 5.78 |
| Invention | 6.41 | 6.46 |

EXAMPLE 5

A health bar was prepared containing powdered dried whole carrot and zucchini as using low shear mixing as follows:

TABLE 5

| Ingredient Number | Ingredient | Percent of Composition |
|---|---|---|
| 1 | Maltrin M-180 | 17.10 |
| 2 | Corn Syrup Solids 36 DE | 15.00 |
| 3 | Corn Bran Fiber | 3.00 |
| 4 | Calcium Carbonate | 1.50 |
| 5 | Apple Powder | 2.40 |
| 6 | Carrot Powder | 17.04 |
| 7 | Zucchini Powder | 3.18 |
| 8 | MCT Oil (Neobeem-5 from Stepan) | 0.60 |
| 9 | Vanilla Powder 10X | 0.06 |
| 10 | Cream S.D. 307737 | 0.22 |
| 11 | Yogurt Spray Dried | 1.00 |
| 12 | Glycerine 99% | 10.00 |
| 13 | Lecithin 3F-UB | 0.30 |
| 14 | High Fructose Corn Syrup 55 | 8.00 |
| 15 | Fat Replacer (Date/Grape/Plum Flavoring) | 10.00 |
| 16 | Crisp Rice 102 | 10.00 |
| 17 | Cinnamon Butter Flavor | 0.60 |

In a Hobart mixer, ingredients 1–11 were mixed for 5 minutes at Speeds 1 and 2. Preblends of ingredients 12 and 13 were then mixed in for 1 minute, and ingredients 14 and 15 were then added to the resulting mix and further blended for 1 minute. Ingredients 16 and 17 were next added and mixed for 1 minute. The resulting mass was removed from the mixer, laid down on a flat surface and rolled to a fairly uniform ½ inch thickness. The mixture was allowed to set at room temperature, and then cut into single serving bars. (If desired, the resulting bars can then be coated with a commercial yogurt preparation.)

EXAMPLE 6

An additional chewy nougat product was made according to the method set forth in Example 1 which delivered 500 mg of calcium, 40 mg of magnesium and 200 I.U.'s of vitamin D3 in a cherry flavor in a 5.3 gram piece according to Table 6 below:

TABLE 6

| Ingredient | Percent of Composition |
|---|---|
| Calcium Carbonate | 23.7% |
| Magnesium Carbonate | 2.9% |
| Corn Syrup Solids | 18.1–27.1% |
| 6X Powdered Sugar | 26.6–35.6% |
| Additional Corn Syrup Solids | 2.6–3.0% |
| Fat Solids (Paramount B) | 5.9% |
| Lecifflin 3F UB | 0.35% |
| Emulsifier (DurEm 117) | 0.25% |
| Sorbitan Stearate (Sorbitan 60K) | 0.25% |
| Vitamin D3* | 2% |
| Glycerin | 3.0% |
| Gum Arabic | 0.4% |
| Gelatin (250 Bloom) | 1.5–1.8% |
| Water | 6–7% |
| Flavorings** | 0.64–1.2% |
| Coloring | 0.01% |
| Acesulfame K (Hoechst) | 0.10% |

*Vitamin D3 was dissolved in a small amount of corn syrup and added with the liquid components.
**Flavorings included the following: Vanilla and Cherry Flavors from various commercial sources.

EXAMPLE 7

A further chewy nougat confectionery product was made according to the method set forth in Example 1 which delivered 500 mg of calcium, 40 mg of magnesium and 200

I.U.'s of vitamin D3 in a cherry flavor in a 5.3 gram piece according to Table 7 below:

TABLE 7

| Ingredient | Percent of Composition |
| --- | --- |
| Calcium Carbonate | 24.5% |
| Magnesium Lactate | 9.6% |
| Corn Syrup Solids | 18.1–27.1% |
| 6X Powdered Sugar | 26.6–35.6% |
| Additional Corn Syrup Solids | 2.6–3.0% |
| Fat Solids (Paramount B) | 4.9% |
| Lecithin 3F UB | 0.30% |
| Emulsifier (DurEm 117) | 0.20% |
| Sorbitan Stearate (Sorbitan 60K) | 0.20% |
| Vitamin D3* | 0.05% |
| Glycerin | 3.0% |
| Gum Arabic | 0.4% |
| Gelatin (250 Bloom) | 1.5–1.8% |
| Water | 6–7% |
| Flavorings** | 0.64–1.2% |
| Coloring | 0.04% |
| Acesulfame K (Hoechst) | 0.10% |

*Vitamin D3 was dissolved in a small amount of corn syrup and added with the liquid components.
**Flavorings included the following: Vanilla and Cherry Flavors from various commercial sources.

In both Examples 6 and 7, the calcium-magnesium chewy nougat confectioneries had a smooth consistency, and were very tasty, with a pronounced cherry flavor.

EXAMPLE 8

In this example, a confectionery power/energy nutrition bar was prepared under low shear conditions having the following ingredients according to Table 8:

TABLE 8

| Ingredient | Percent of Composition |
| --- | --- |
| Fat Soluble Vitamins A, D3, E | 0.21% |
| Water Soluble Vitamins (B complex with Folic Acid) | 0.01% |
| Vitamin C (Ascorbic Acid) | 0.15% |
| Niacinamide | 0.04% |
| Biotin | 0.07% |
| Calcium D-Panthothenate | 0.025% |
| Minerals* | 4.7% |
| Fructose Powder | 20–21% |
| Dutch Processed Coca Powder | 11% |
| Corn Syrup Solids | 11–12% |
| Fat Solids | 5.5% |
| Emulsifier (Myvacet 707) | 0.8% |
| Protein (Whey, Caseinate & ARCONS) | 25% |
| Fiber (Solka Floc) | 2.8% |
| Sorbitol | 2.5% |
| Glycerin | 6–7% |
| Gum Arabic | 0.2% |
| Gelatin (250 Bloom) | 1.0% |
| Water | 6–7% |
| Flavorings** | 0.64–1.5% |
| Coloring | 0.04% |
| Aspartame | 0.10% |

*Included iron, copper, zinc, calcium, magnesium and manganese encapsulated using a combination of Myvacet 707, Stearine D-17 and DurEm 117 in an approximate 1:4 ration.
**One or more of butter, cream, vanilla, chocolate, almond and rasberry flavors.

EXAMPLE 9

In this example, a multi-vitamin soft chew confectionery was prepared under low shear conditions (using a Sigma mixer) having the following ingredients according to Table 9. Hydrobinding component (water, gelatin, glycerin, gum arabic) were combined together and added last to the final mixture:

TABLE 9

| Ingredient | Percent of Composition |
| --- | --- |
| Vitamin B Complex Encapsulation* | 0.75% |
| Vitamin A Palmitate | 0.37% |
| Vitarnin E Acetate | 1.50% |
| Niacinamide | 0.22% |
|  | 0.05% |
| Confectioners Sugar 6X Powder | 43% |
| Maltodextrin | 11–12% |
| Corn Syrup Solids | 18% |
| Ascorbic Acid | 0.7% |
| Lecithin | 0.7% |
| Citric Acid | 0.7% |
| Non-fat Dry Milk Powder | 5% |
| Sorbitol | 1.5% |
| Glycerin, 99%, USP | 3–4% |
| Gum Arabic | 0.55% |
| Gelatin Type B (250 Bloom) | 2.0% |
| Water | 4.8% |
| Flavorings** | 1.0–1.5% |
| Coloring | 0.1% |
| Xylitol | 2.5% |
| MCT Oil | 10% |

*Included thiamine, riboflavin, B6, B12 and biotin encapsulated with.
**One or more of vanillin, cream and orange flavors, and orange oil. Each 5.3 gram piece supplied approximately 25% U.S. RDA of vitamins.

EXAMPLE 10

For a further understanding of the present invention the following additional example (with Table 10) is provided to illustrate the unique methods of making a confectionery mass and product resulting therefrom. Unless otherwise specified, percentages of components in the composition are given as percentage by weight (wt %). Also, unless otherwise indicated, all materials were obtained from commercial suppliers:

TABLE 10

| Component | Qty % in Final |
| --- | --- |
| Confectioner's Sugar 6X Powder | 30–35 |
| Maltodextrin | 30–35 |
| Cocoa Powder | 8 |
| Sorbitol | 5 |
| Xylitol | 1 |
| Flavor* | 2 |
| Aspartame | 0.12 |
| Acesulfame Potassium | 0.10 |
| Partially Hydrogenated Soybean Oil | 4 |
| Lecithin | 1 |
| Tap Water | 6 |
| Gelatin Type B 250 Bloom | 1.8 |
| Glycerin 99% | 3 |
| Gum Arabic | 0.4 |
| Caffeine Encapsulation** | 3.5 |

*included cream flavor, vanilla powder and natural and artificial chocolate flavor.
**included the following: caffeine powder (35%), fat (Stearine 17) (38%), emulsifier (Myvacet 707) (2.5%), cocoa powder and/or coffee//coffee flavor (11%), food-grade wax (10%) and artificial sweetener (aspartame) (3.5%).

The foregoing components were mixed under low shear conditions to yield a sweet-tasting, chewy confectionery which delivered 60 mg. of caffeine in a single-size dose (about 5–6 grams).

Thus, while there have been described what are primarily believed to be the preferred embodiments, those skilled in the art well appreciate that other and further changes and modifications can be made without departing from the true spirit of the invention, and it is intended to include all such changes and modifications within the scope of the claims which are appended hereto.

We claim:

1. An uncooked, unspun intimately mixed confectionery composition having sufficient internal cohesivity to be handled without losing its integrity as a mass, said composition being substantially free of unbound water and having substantially no phase separation of moisture, comprising:
   (i) a saccharide-based component;
   (ii) a hydrated hydrobinding component, said composition having a water activity less than about 0.60%, and being hydrated sufficiently to provide controlled water delivery to the saccharide-based component to provide only enough moisture to bind the ingredients together when mixed and provide internal lubricity for imbibing, delivering and maintaining the moisture in the mass to provide internal cohesivity without losing its integrity as a mass, said hydrated hydrobinding component comprising at least one material selected from the group consisting of proteinaceous material, food grade gums and combinations thereof to impart viscoelasticity to the composition, wherein component (i) is present between about 30–99.5% by weight and component (ii) is present between about 0.5–20% by weight of said composition.

2. The composition of claim 1, wherein the water activity of said composition is less than about 0.55%.

3. The composition of claim 2, wherein said bioaffecting agent is selected from the group consisting of calcium, wherein said calcium is substantially untreated with either liquid or oil, said calcium comprising at least about 20% by weight of said composition.

4. The composition of claim 1 or 2 further comprising a bioaffecting agent, food, nutritional component, dietary soluble or insoluble fiber, vitamin or mineral for effecting a biological and/or chemical response in the body.

5. The composition of claim 4, wherein said mineral is calcium.

6. The composition of claim 5, wherein said calcium is present in an amount of at least about 20% by weight of said composition.

7. The composition of claim 6, wherein said calcium is present in an amount of at least about 23% by weight of said composition.

8. The composition of claim 7, wherein said calcium is present in an amount of up to about 40% by weight of said composition.

9. The composition of claim 4, wherein said calcium is calcium carbonate.

10. The composition of claim 4, wherein said calcium is substantially dry.

11. The composition of claim 10, wherein said calcium is not pre-coated.

12. The composition of claim 11, wherein said proteinaceous material is gelatin.

13. The composition of claim 1 or 2 further comprising a cross-linking agent mixed with said hydrobinding component.

14. The composition of claim 1 or 2 further comprising an aerating agent selected from the group consisting of egg whites, soy protein and combinations thereof.

15. The composition of claim 1 or 2 wherein the hydrobinding component includes between about 0.1–10% of a wetting agent or softening humectant.

16. The composition of claim 1 or 2 wherein said confectionery is a chewy nougat with shearform matrix characteristics.

17. A method of making an uncooked, unspun intimately mixed composition having sufficient internal cohesivity to be handled without losing its integrity as a mass, the composition being substantially free of unbound water and having no phase separation of moisture but which has only enough moisture present to bind the components together, comprising shear mixing together without cooking or spinning:
   (i) a substantially dry saccharide based component; and
   (ii) a hydrobinding component, said hydrobinding component being hydrated prior to combining with said saccharide-based component, said composition having a water activity less than about 0.60%, and being hydrated sufficiently to provide controlled water delivery to the uncooked saccharide-based component to provide only enough moisture to bind the ingredients together when mixed and provide internal lubricity for imbibing, delivering and maintaining the moisture in the mass to provide internal cohesivity without losing its integrity as a mass, said hydrobinding component comprising a proteinaceous material selected from gelatin, food grade gums and combinations thereof, wherein said component (i) is present between about 30–99.5% by weight, said component (ii) is present between about 0.5–20% of said composition.

18. The process of claim 17 wherein the water activity of component (ii) is less than about 0.55% and bioaffecting agent is present between about 0.1–50% of said composition.

19. The process of claim 17 or 18, further comprising shear mixing without cooking or spinning a bioaffecting agent into the mixture.

20. The method of claim 19, wherein said bioaffecting agent is untreated and is at least one member selected from the group consisting of a food or nutritional component, dietary soluble or insoluble fiber, vitamin or mineral for effecting a biological and/or chemical response in the body.

21. The method of claim 20, wherein said bioaffecting agent is a bioassimilable source of calcium.

22. The method of claim 21, wherein said calcium is combined with said saccharide-based component in substantially dry form prior to mixing with said hydrobinding component.

23. The method of claim 17 or 18 wherein said shear mixing is high shear mixing, low shear mixing, or a combination thereof.

24. The method of claim 23, wherein said shear mixing imparts shearform matrix characteristics to said composition.

25. The method of claim 24, wherein said composition is a chewy nougat confectionery which is storage stable.

26. The method of claim 25, wherein said hydrobinding component is hydrated sufficiently to provide internal lubricity without phase separation.

27. The method of claim 26, wherein said saccharide-based component is high shear mixed with said bioaffecting agent to produce an admixture, said admixture then being low shear mixed with said hydrobinding component.

28. The method of claim 17 or 18 wherein a cross-linking agent is mixed with said hydrobinding component.

29. The method of claim 17 or 18 wherein said hydrobinding component further comprises between about 0.1–10% of a wetting agent or softening agent.

30. The method of claim 17 or 18 wherein said bioaffecting agent is at least one member selected from the group consisting of vitamins, minerals, nutraceuticals, protein and dietary fiber.

31. The method of claim 30, wherein said bioaffecting agent is at least about 23% by weight of calcium.

32. The method of claim 30, wherein said bioaffecting agent is effectively taste-masked by said method.

* * * * *